United States Patent
Hoffer et al.

(10) Patent No.: US 10,898,326 B2
(45) Date of Patent: Jan. 26, 2021

(54) CRIMPING HEART VALVE WITH NITINOL BRAID

(71) Applicant: St. Jude Medical, Cardiology Division, Inc., St. Paul, MN (US)

(72) Inventors: Nathaniel Hoffer, Princeton, MN (US); John Matejka, Crystal, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 161 days.

(21) Appl. No.: 16/176,437

(22) Filed: Oct. 31, 2018

(65) Prior Publication Data

US 2019/0254819 A1     Aug. 22, 2019

Related U.S. Application Data

(60) Provisional application No. 62/632,479, filed on Feb. 20, 2018.

(51) Int. Cl.
*A61F 2/24* (2006.01)
*A61F 2/95* (2013.01)

(52) U.S. Cl.
CPC .......... *A61F 2/2436* (2013.01); *A61F 2/2418* (2013.01); *A61F 2/2427* (2013.01);
(Continued)

(58) Field of Classification Search
CPC ........ A61F 2/2418; A61F 2/2427; A61F 2/95; A61F 2/962; A61F 2/2433; A61F 2/2436; A61F 2002/9511; A61F 2002/9505
See application file for complete search history.

(56) References Cited

U.S. PATENT DOCUMENTS

| | | |
|---|---|---|
| 3,657,744 A | 4/1972 | Ersek |
| 4,423,730 A | 1/1984 | Gabbay |

(Continued)

FOREIGN PATENT DOCUMENTS

| | | |
|---|---|---|
| DE | 102005003632 A1 | 8/2006 |
| EP | 1129744 A1 | 9/2001 |

(Continued)

OTHER PUBLICATIONS

Quaden, et al., "Percutaneous Aortic Valve Replacement: Resection Before Implantation", European Journal of Cardio-Thoracic Surgery, vol. 27, No. 5, May 2005, pp. 836-840.

(Continued)

*Primary Examiner* — Tuan V Nguyen
(74) *Attorney, Agent, or Firm* — Lerner, David, Littenberg, Krumholz & Mentlik, LLP

(57) ABSTRACT

A system for crimping a fully deployed heart valve includes a delivery tube extending in a longitudinal direction and having a lumen for receiving the crimped heart valve, a deployment device including a first member and a second member moveably secured to the first member, and a sheath configured to at least partially enclose a radially collapsible stent. A first attachment area of the sheath is connected to the first member and a second attachment area of the sheath is connected to the second member such that movement of the first member relative to the second member tensions the sheath for crimping the heart valve. A method of crimping a fully deployed heart valve is also provided.

20 Claims, 6 Drawing Sheets

(52) U.S. Cl.
CPC .............. *A61F 2/95* (2013.01); *A61F 2/2439* (2013.01); *A61F 2/9522* (2020.05); *A61F 2002/9528* (2013.01); *A61F 2002/9534* (2013.01); *A61F 2210/0014* (2013.01); *A61F 2220/0025* (2013.01); *A61F 2220/0075* (2013.01); *A61F 2220/0083* (2013.01)

(56) References Cited

U.S. PATENT DOCUMENTS

| | | | |
|---|---|---|---|
| 5,078,720 | A | 1/1992 | Burton et al. |
| 5,415,664 | A | 5/1995 | Pinchuk |
| 5,484,444 | A | 1/1996 | Braunschweiler et al. |
| 5,702,418 | A | 12/1997 | Ravenscroft |
| 5,824,041 | A | 10/1998 | Lenker et al. |
| 5,843,167 | A | 12/1998 | Dwyer et al. |
| 5,924,424 | A | 7/1999 | Stevens et al. |
| 5,968,068 | A | 10/1999 | Dehdashtian et al. |
| 5,980,533 | A | 11/1999 | Holman |
| 6,077,297 | A | 6/2000 | Robinson et al. |
| 6,269,819 | B1 | 8/2001 | Oz et al. |
| 6,306,141 | B1 | 10/2001 | Jervis |
| 6,391,050 | B1 | 5/2002 | Broome |
| 6,468,299 | B2 | 10/2002 | Stack et al. |
| 6,623,518 | B2 | 9/2003 | Thompson et al. |
| 6,814,746 | B2 | 11/2004 | Thompson et al. |
| 6,830,584 | B1 | 12/2004 | Seguin |
| 7,018,406 | B2 | 3/2006 | Seguin et al. |
| 7,311,730 | B2 | 12/2007 | Gabbay |
| 7,510,572 | B2 | 3/2009 | Gabbay |
| 7,682,390 | B2 | 3/2010 | Seguin |
| 7,803,185 | B2 | 9/2010 | Gabbay |
| 8,562,663 | B2 | 10/2013 | Mearns et al. |
| 8,840,663 | B2 | 9/2014 | Salahieh et al. |
| 9,192,469 | B2 | 11/2015 | Mearns et al. |
| 9,241,794 | B2 | 1/2016 | Braido et al. |
| 9,414,914 | B2 | 8/2016 | Duffy et al. |
| 9,414,917 | B2 | 8/2016 | Young et al. |
| 2003/0050694 | A1 | 3/2003 | Yang et al. |
| 2004/0210304 | A1 | 10/2004 | Seguin et al. |
| 2004/0215315 | A1* | 10/2004 | Jones .................. A61L 31/16 623/1.11 |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2006/0074484 | A1 | 4/2006 | Huber |
| 2006/0106415 | A1 | 5/2006 | Gabbay |
| 2006/0142848 | A1 | 6/2006 | Gabbay |
| 2006/0167468 | A1 | 7/2006 | Gabbay |
| 2006/0259120 | A1 | 11/2006 | Vongphakdy et al. |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0073391 | A1 | 3/2007 | Bourang et al. |
| 2007/0088431 | A1 | 4/2007 | Bourang et al. |
| 2007/0112422 | A1 | 5/2007 | Dehdashtian |
| 2007/0162100 | A1 | 7/2007 | Gabbay |
| 2007/0168013 | A1 | 7/2007 | Douglas |
| 2007/0203575 | A1 | 8/2007 | Forster et al. |
| 2007/0239271 | A1 | 10/2007 | Nguyen |
| 2007/0244552 | A1 | 10/2007 | Salahieh et al. |
| 2008/0071369 | A1 | 3/2008 | Tuval et al. |
| 2008/0147182 | A1 | 6/2008 | Righini et al. |
| 2009/0054975 | A1 | 2/2009 | del Nido et al. |
| 2009/0171456 | A1* | 7/2009 | Kveen .................. A61F 2/2433 623/2.11 |
| 2010/0004740 | A1 | 1/2010 | Seguin et al. |
| 2010/0286768 | A1 | 11/2010 | Alkhatib |
| 2010/0298931 | A1 | 11/2010 | Quadri et al. |
| 2011/0190865 | A1* | 8/2011 | McHugo .................. A61F 2/95 623/1.11 |
| 2011/0224678 | A1 | 9/2011 | Gabbay |
| 2013/0178888 | A1 | 7/2013 | Bliss et al. |
| 2014/0214153 | A1 | 7/2014 | Ottma et al. |
| 2014/0331475 | A1 | 11/2014 | Duffy et al. |
| 2015/0238315 | A1* | 8/2015 | Rabito .................. A61F 2/2436 623/2.11 |
| 2015/0282821 | A1 | 10/2015 | Look et al. |
| 2016/0206426 | A1 | 7/2016 | Khoynezhad et al. |
| 2016/0278955 | A1 | 9/2016 | Liu et al. |
| 2016/0324633 | A1 | 11/2016 | Gross et al. |
| 2017/0165066 | A1* | 6/2017 | Rothstein .............. A61F 2/2418 |
| 2017/0273787 | A1* | 9/2017 | Passman .............. A61F 2/2436 |
| 2017/0325830 | A1 | 11/2017 | Martin et al. |

FOREIGN PATENT DOCUMENTS

| | | |
|---|---|---|
| EP | 1157673 A2 | 11/2001 |
| EP | 1926455 A2 | 6/2008 |
| WO | 02067782 A2 | 9/2002 |
| WO | 07071436 A2 | 6/2007 |
| WO | 08070797 A2 | 6/2008 |
| WO | 10051025 A1 | 5/2010 |
| WO | 10087975 A1 | 8/2010 |

OTHER PUBLICATIONS

Ruiz, et al, "Overview of Pre-CE Mark Transcatheter Aortic Valve Technologies", Euro PCR, May 2010, 14 pages.
ESSR for EP Application No. 18204261.4 dated May 10, 2019.

* cited by examiner

CRIMPING HEART VALVE WITH NITINOL BRAID

CROSS-REFERENCE TO RELATED APPLICATIONS

This application claims the benefit of the filing date of U.S. Provisional Patent Application No. 62/632,479 filed Feb. 20, 2018, the disclosure of which is hereby incorporated herein by reference.

BACKGROUND OF THE INVENTION

The present invention relates to collapsible prosthetic heart valve implantation, and more particularly, to apparatus and methods for collapsing prosthetic heart valves during an implantation procedure.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to its full operating size. For balloon-expandable valves, this generally involves releasing the entire valve, assuring its proper location, and then expanding a balloon positioned within the valve stent. For self-expanding valves, on the other hand, the stent automatically expands as the stent is withdrawn from the delivery apparatus.

In conventional delivery systems for self-expanding aortic valves, the annulus end of the valve is typically unsheathed (withdrawn from the delivery apparatus) and expanded first, to test the basic functionality of the valve, while the aortic end of the valve remains sheathed. Afterwards, a user (such as an interventional cardiologist or a physician) may desire to withdraw or reposition the stent within a patient's aortic annulus. To accomplish this, the user may re-sheath the annulus end, thereby crimping the valve for repositioning. After the valve has been repositioned, the user can again deploy the valve.

In conventional systems, once a self-expanding valve has been fully deployed, or fully unsheathed, it expands to a diameter larger than that of the delivery apparatus that previously contained the valve in the collapsed condition, making re-sheathing impossible, or difficult at best. Thus, conventional delivery systems allow for re-sheathing only after partial deployment, which limits the user's ability to test valve function and fitment.

It is not currently possible, using conventional delivery devices, to determine whether a valve assembly will function as intended without full deployment of die heart valve. Moreover, it has been observed that full deployment sometimes causes the valve to "jump" or reposition when the aortic end engages with tissue. In these instances, where the valve includes a malfunction or has moved to an improper position after the valve has been fully deployed, the heart valve would need to be entirely removed from the patient. Removing a fully deployed heart valve requires surgery and greatly increases the risk of damaging the surrounding tissue of an already at risk patient.

There therefore is a need for further improvements to the systems and methods for transcatheter delivery of collapsible prosthetic heart valves, and in particular, self-expanding prosthetic heart valves. Among other advantages, the present invention addresses these needs by providing a system for re-crimping the valve after it has been fully deployed.

BRIEF SUMMARY OF THE INVENTION

In accordance with a first aspect of the present invention, a system for crimping a heart valve during an implantation procedure is provided. The system advantageously allows for crimping of the valve after it has been fully deployed, and thus, allows a physician to replace the valve if it is not functioning properly and/or reposition the valve if proper fitment has not been achieved.

One embodiment of the system includes a delivery tube extending in a longitudinal direction and defining a hollow lumen for receiving the heart valve, a deployment device including a first member and a second member moveably secured to the first member, and a sheath configured to at least partially surround a radially collapsible stent. The attachment device of the first member is attachable to a first attachment area of the sheath and the attachment device of the second member is attachable to a second attachment area of the sheath such that movement of the first member relative to the second member provides a tensioning force on the sheath for crimping the heart valve. The sheath may be formed of nitinol and be at least partially coated with a lubricant.

The first attachment area of the sheath is provided adjacent a proximal end of the sheath and the second attachment area of the sheath is provided adjacent a distal end of the sheath. Furthermore, the first attachment area and second attachment area may include at least one loop for cooperating with the at least one of a hook, a clamp, and a tether provided on at least one of the first member and the second member. The tether may be a breakable tether.

In a preferred embodiment, the second member is telescopingly arranged within the first member for transitioning the deployment device between a first condition, in which the first member and the second member define a first length, and a second condition, in which the first member and the second member define a second length greater than the first length.

The heart valve includes a stent formed of a plurality of struts. The stent is transitionable between a radially collapsed state and a radially expanded state, such that in the expanded state, a diameter of the stent is larger than a diameter of the lumen of the delivery tube. The stent also includes a valve including a cuff and at least one leaflet. When the deployment device is transitioned from the first condition to the second condition, tension is applied to the sheath for radially compressing at least a portion of the stent.

The system further includes a first wire and a second wire opposingly secured within the deployment device for guiding delivery of the heart valve.

Also provided herein is a method for crimping a heart valve after the heart valve has been fully deployed from a delivery tube. The method includes moving a first member connected to a sheath at a first location away from a second member connected to the sheath at a second location when the sheath at least partially encloses a stent configured to transition between a radially collapsed state and a radially expanded state. This movement applies a tensioning force to the sheath to radially engage the stent and transition the stent from the expanded state to the collapsed state. In a preferred embodiment, moving the first member away from the second member includes a telescoping movement.

In the collapsed state, a user may manipulate at least one of a plurality of wires disposed within the first and second members to reposition the heart valve to a new location. Additionally, or alternatively, after at least a portion of the heart valve is crimped to a diameter that is smaller than a diameter of a lumen of the delivery tube, the valve may be recaptured within the lumen of the delivery tube. At least one of the first member and the second member may then be disconnected from the sheath and the first member, second member, and the delivery device may be withdrawn from the body of a patient.

In certain aspects of the invention, only one of the first member and the second member is disconnected from the sheath. Thus, in one aspect of the invention, the sheath remains in the body after withdrawal of the delivery device and in other aspects of the invention the sheath is removed from the body along with the delivery device.

BRIEF DESCRIPTION OF THE DRAWINGS

Various embodiments of a delivery system are disclosed herein with reference to the drawings, wherein.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "trailing" and "leading" are to be taken as relative to the user of the delivery devices. "Trailing" is to be understood as relatively close to the operator, and "leading" is to be understood as relatively farther away from the operator.

Figure 1:
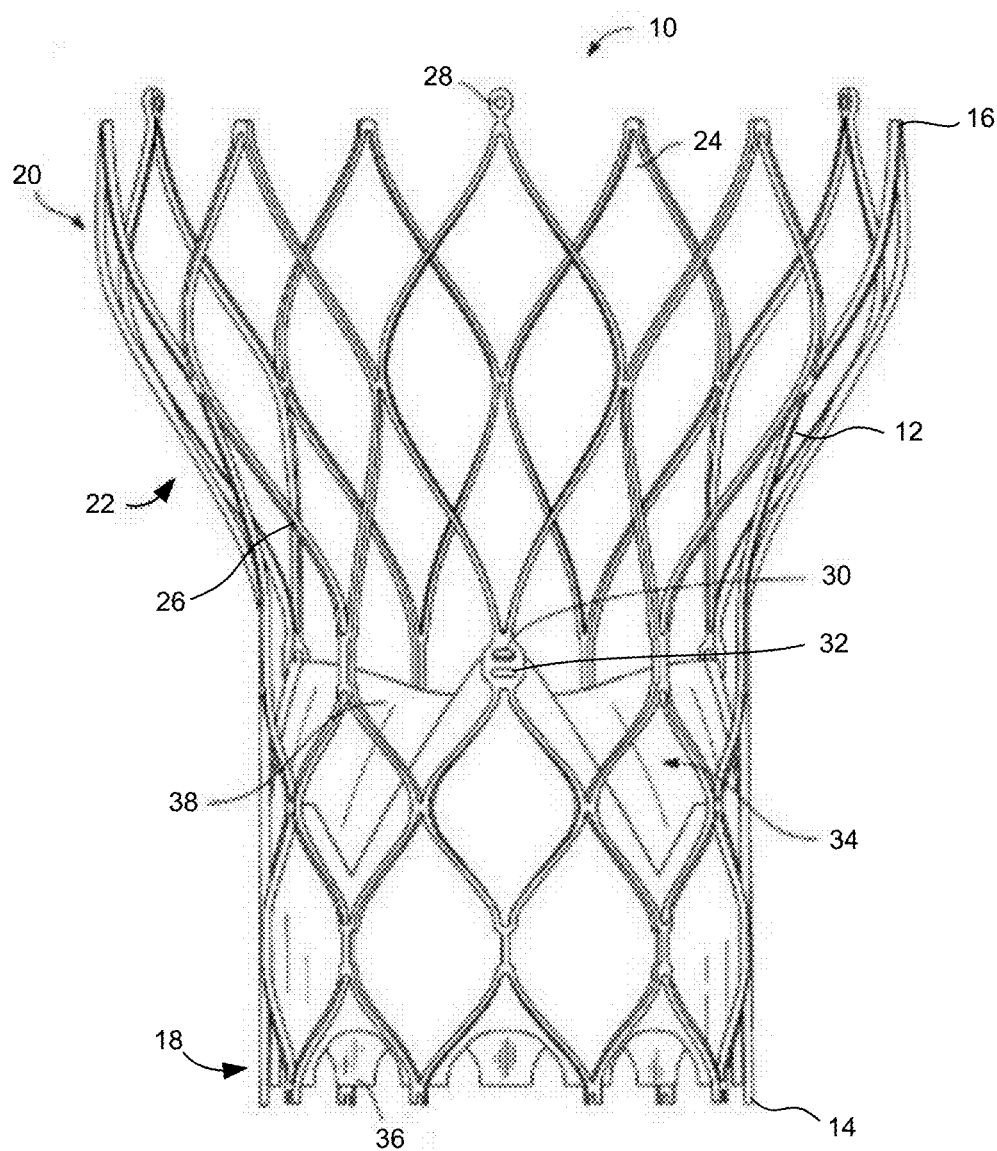
FIG. 1 is a partial side elevational view of a collapsible prosthetic heart valve.

FIG. 1 shows a collapsible prosthetic heart valve 10 according to an embodiment of the present disclosure. The prosthetic heart valve 10 is designed to replace the function of the native aortic valve of a patient. Examples of collapsible prosthetic heart valves are described in U.S. Pat. Nos. 7,018,406 and 9,241,794, the disclosures of both of which are hereby incorporated herein by reference.

Prosthetic heart valve 10 includes an expandable stent 12 which may be formed from biocompatible materials that are capable of self-expansion, for example, shape memory alloys such as nitinol. Stent 12 extends from a distal or annulus end 14 to a proximal or aortic end 16, and includes an annulus section 18 adjacent distal end 14 and an aortic section 20 adjacent proximal end 16. Annulus section 18 has a relatively small cross-section in the expanded state compared to aortic section 20 in the expanded state. Preferably, annulus section 18 is in the form of a cylinder having a substantially constant diameter along its length. A transition section 2:2 tapers outwardly from annulus section 18 to aortic section 20. Each of the sections of stent 12 includes a plurality of cells 24 formed of a plurality of struts 26 connected to one another to form one or more annular rows around the stent. In one particular embodiment, shown in FIG. 1, annulus section 18 may have two annular rows of complete cells and aortic section 20 and transition section 22 may each have one or more annular rows of partial cells. Cells 24 in aortic section 20 may be larger than cells 24 in annulus section 18. The larger cells in the aortic section 20 facilitate positioning of prosthetic valve 10 without stent 12 interfering with blood flow to the coronary arteries.

Stent 12 may include one or more retaining elements 28 provided on aortic section 20 and sized and shaped to cooperate with a delivery device. Engagement of retaining elements 28 with a corresponding retaining structure on the delivery device maintains prosthetic heart valve 10 in the crimped position within the delivery device, minimizes longitudinal movement of the prosthetic heart valve relative to the delivery device during unsheathing or resheathing procedures, and prevents rotation of the prosthetic heart valve relative to the delivery device as the delivery device is advanced to the target location and during deployment.

Stent 12 may also include a plurality of commissure features 30 for attaching the commissure between two adjacent leaflets to stent 12. As is shown in FIG. 1, commissure features 30 may lie at the intersection of four cells 24, two of the cells being adjacent one another in the same annular row, and the other two cells being in different annular rows and lying in an end-to-end relationship. Preferably, commissure features 30 are positioned entirely within annulus section 18 or at the juncture of annulus section 18 and transition section 22. Commissure features 30 may include one or more eyelets 32 which facilitate the suturing of the leaflet commissure to stent 12.

Prosthetic heart valve 10 includes a valve assembly 34 preferably positioned in annulus section 18. Valve assembly 34 may be secured to stent 12 by suturing valve assembly 34 to struts 26 and/or to commissure features 30. Valve assembly 34 includes a cuff 36 and a plurality of leaflets 38 which open and close collectively to function as a one-way valve.

Since FIG. 1 illustrates a prosthetic heart valve for replacing a native tricuspid valve, such as the aortic valve, prosthetic heart valve 10 is illustrated with three leaflets 38, as well as three commissure features 30. However, it will be appreciated that prosthetic heart valves according to this aspect of the invention may have a greater or lesser number of leaflets 38 and/or commissure features 30.

Although cuff 36 is illustrated in FIG. 1 as being disposed on the luminal or inner surface of annulus section 18, it is contemplated that cuff 36 may be disposed on the abluminal or outer surface of annulus section 18, or may cover all or part of either or both of the luminal and abluminal surfaces of annulus section 18. Both cuff 36 and leaflets 38 may be wholly or partly formed of any suitable biological material, such as bovine or porcine pericardium, or polymers, such as PTFE, urethanes and the like.

As is shown in FIG. 1, the entirety of valve assembly 34, including the leaflet commissures, is positioned in annulus section 18 of stent 12. That is, the entire valve assembly 34 is substantially positioned between distal end 14 of stent 12 and commissure features 30, such that none of valve assembly 34 is positioned between commissure features 30 and proximal end 16 of stent 12. As is explained in further detail hereinafter, this configuration is particularly advantageous during conventional delivery (illustrated in FIGS. 3 and 4B) for enabling the deployment of heart valve 10 by an amount sufficient for valve leaflets 38 to operate, while proximal end 16 of stent 12 remains collapsed within the delivery device. Since the present invention provides a device for recapturing heart valve 10 after it has been fully deployed, the location of valve assembly 34 need not be limited exclusively to annulus section 18. For example, valve assembly 34 may extend into transition section 22.

Prosthetic heart valve 10 described above may be used to replace a native heart valve, such as the aortic valve, a surgical heart valve, or a heart valve that has undergone a surgical procedure. Prosthetic heart valve 10 may be delivered to the desired site (e.g., near a native aortic annulus) using the delivery device described in detail below. During delivery, prosthetic heart valve 10 is disposed inside the delivery device in the collapsed condition. The delivery device may be introduced into a patient using a transfemoral, transapical, transseptal approach or another approaoch. Once the delivery device has reached the target site, the user may deploy prosthetic heart valve 10. Upon deployment, the prosthetic heart valve expands into secure engagement within the native anatomic structure such as the aortic annulus. When the prosthetic heart valve is properly positioned inside the patient, it works as a one-way valve, allowing blood to flow in one direction and preventing blood from flowing in the opposite direction.

Figure 2:
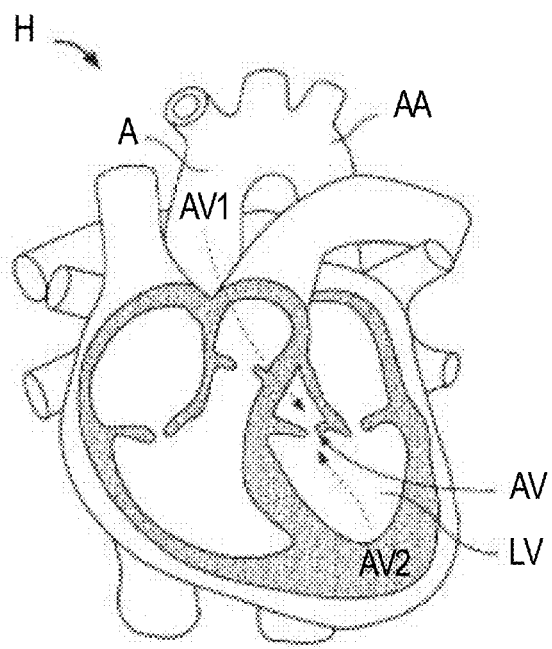
FIG. 2 is a highly schematic cutaway view of the human heart, showing two approaches for delivering a prosthetic aortic heart valve.

FIG. 2 illustrates a human heart H and two different approaches of delivering prosthetic heart valve 10 to its intended target at aortic valve AV. As illustrated in FIG. 2, heart H includes an aorta A, an aortic arch AA and a left ventricle LV. Two separate paths are shown for introducing prosthetic heart valve 10 to aortic valve AV.

A transfemoral approach of the prosthetic heart valve is indicated by the dashed arrow and the label "AV1". In this method, prosthetic heart valve 10 is inserted into the femoral artery, tracked through the vasculature and then introduced to the target site via the aortic arch AA. Echocardiography and other means may be used to help guide the delivery device through this approach.

A second dashed arrow, labeled "AV2," indicates a transapical approach of the prosthetic valve. In transapical delivery, a small incision is made between the ribs and into the apex of left ventricle LV to deliver the prosthetic heart valve to the target site.

Figure 3:
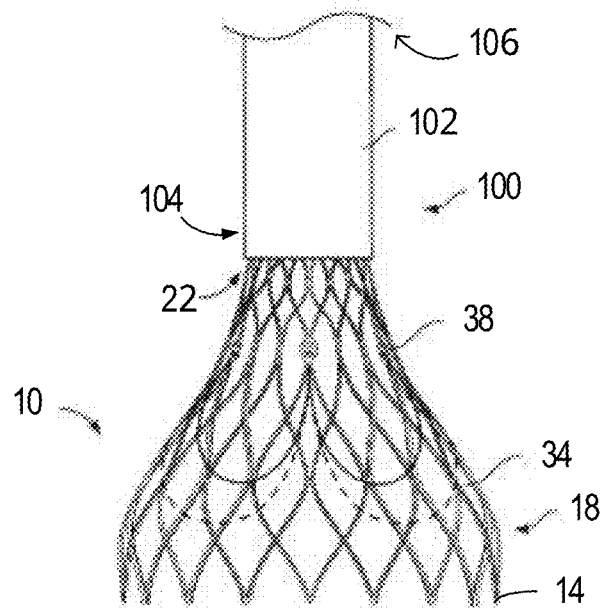
FIG. 3 is a fragmentary side elevational view showing partial deployment of a collapsible prosthetic heart valve from a delivery device using a transfemoral approach.

FIG. 3 illustrates a conventional device 100 for transfemoral delivery of a prosthetic heart valve. In the transfemoral approach, the leading end of a delivery tube 102 points in the distal direction of the heart. Prior to deployment, valve 10 is disposed in delivery tube 102 with annulus section 18 closest to leading end 104 of delivery tube 102. As seen in FIG. 3, the transfemoral approach first unsheathes annulus end 18 of heart valve 10, allowing annulus section 18 to expand prior to full deployment of valve 10. For example, delivery tube 102 may be retracted toward its trailing end 106 while internal components (not shown) of delivery tube 102 hold heart valve 10 stationary. More specifically, proximal or aortic end 16 of valve 10, including aortic section 20, remains partially sheathed and coupled to delivery tube 102, while distal or annulus end 14 of the valve, including annulus section 18, expands. It will be appreciated that valve assembly 34, and specifically the function of leaflets 38, may be preliminarily tested in this approach without fully deploying heart valve 10.

In other circumstances, it may be desirable to use a transapical approach (shown as "AV2" in FIG. 2) as opposed to the transfemoral approach (shown as "AV1" in FIG. 2). For example, calcification in arteries may render tracking of the delivery device using a transfemoral approach difficult and make a transapical approach the preferable route.

Figure 4:
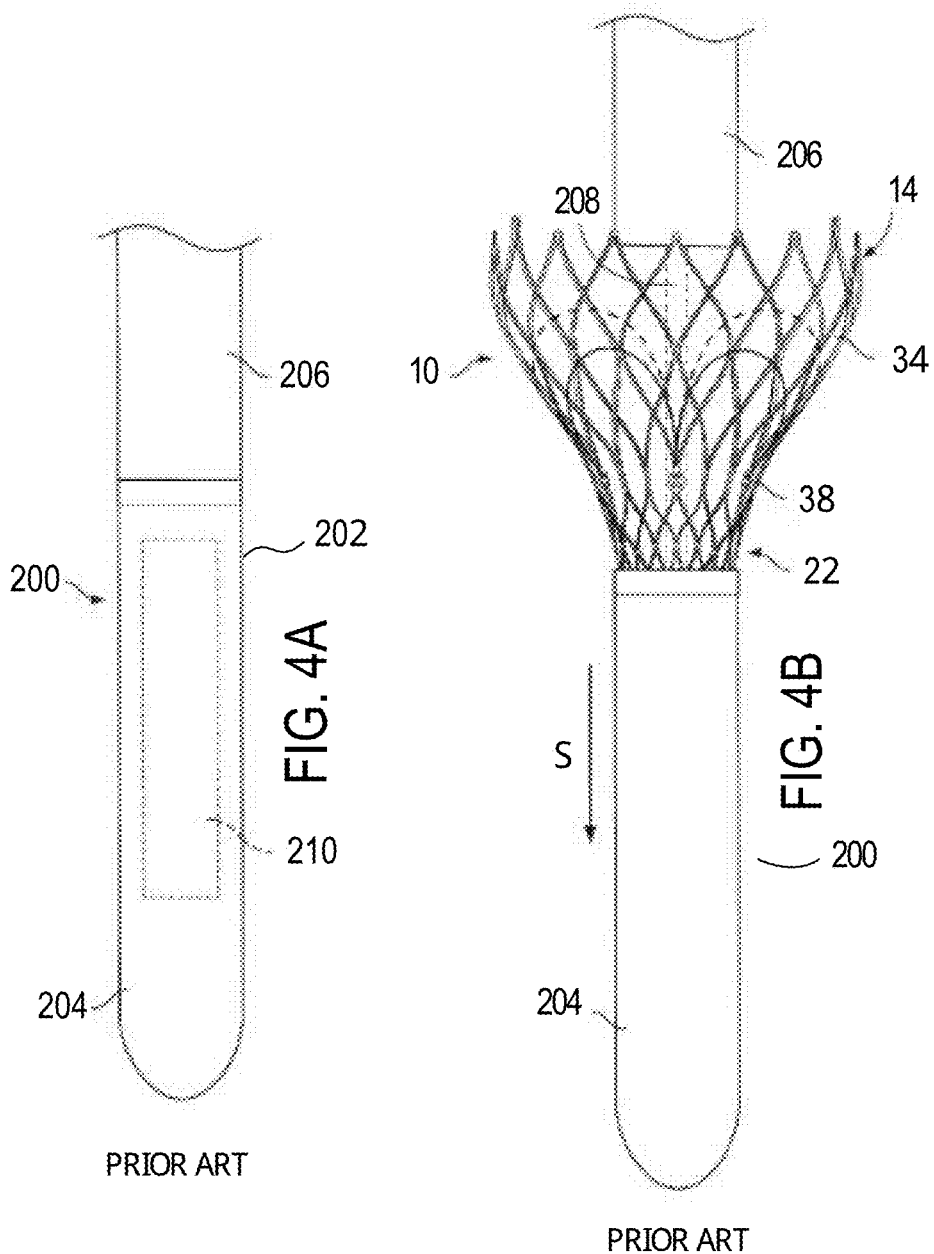
FIG. 4A is a fragmentary side elevational view of a conventional delivery device for use with a transapical approach.
FIG. 4B is a fragmentary side elevational view of the delivery device of FIG. 4A showing partial deployment of a collapsible prosthetic heart valve using the transapical approach.

FIGS. 4A and 4B illustrate a conventional delivery device 200 used for a transapical approach. Delivery device 200 includes a delivery tube 202 having a leading end 204 connected to a trailing end 206 via a support core 208. Delivery tube 202 defines a compartment 210 for housing prosthetic heart valve 10.

During delivery, delivery device 200 is advanced in a forward direction through the apex of the heart and into the aorta until annulus end 14 of valve 10 is disposed at or near the annulus of the native valve and leading end 204 of delivery device 200 projects through the native valve into the aorta. While trailing end 206 of delivery device 200 is held stationary, leading end 204 is translated in a forward direction (depicted by arrow "S") away from trailing end 206 to remove prosthetic heart valve 10 from compartment 210. In this configuration, aortic section 20 of valve 10 remains disposed in delivery tube 202 while annulus section 18 expands after it has been unsheathed. Thus, trailing-end-first deployment deploys annulus section 18 before aortic section 20. The deployment process can be reversed before full deployments, by reversing the movement of leading end 204 of delivery device 200 relative to stent 10.

Irrespective of whether a transfemoral or transapical approach is utilized, conventional delivery requires that aortic section 20 remain at least partially sheathed by delivery tube 102, 202 in order for valve 10 to be subsequently re-crimped. However, to test valve assembly 34 in a fully expanded position, and because heart valve 10 can "jump" or reposition upon full deployment, which can alter fitment and lead to PV leak, it would be desirable to be able to re-crimp heart valve 10 for repositioning or withdrawing the valve after stent 12 has been frilly deployed.

Figure 5:
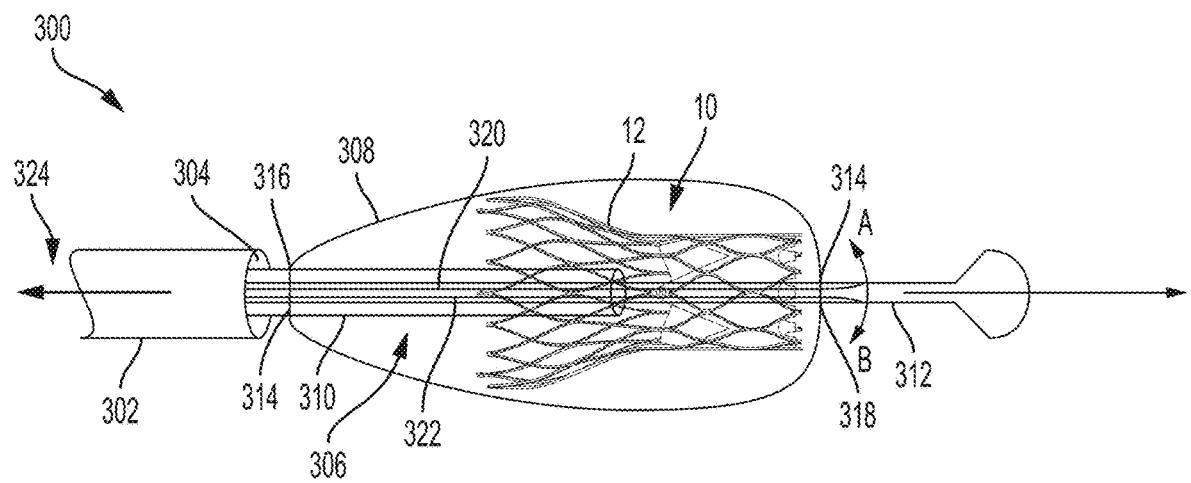
FIG. 5 is a fragmentary side-view of a crimping system in accordance with an embodiment of the present invention including a fully deployed prosthetic heart valve.

FIG. 5 illustrates one embodiment of system 300, which allows prosthetic heart valve 10 to be crimped, and thus repositioned, after valve 10 has been fully deployed. As used herein, the term "full deployment" means the entire heart valve has been withdrawn from the delivery device and transitioned to its expanded state.

Delivery device 300 includes delivery tube 302 having a lumen 304, a deployment device 306 for controlling the crimping of prosthetic heart valve 10, and a tensionable, braided sheath 308 for compressing heart valve 10 after full deployment (the braided portion of sheath 308 has been omitted from FIG. 5 for clarity).

Delivery tube 302 may be any tube-like delivery device such as a catheter, a trocar, a laparoscopic instrument, or the like, configured to house prosthetic heart valve 10 in a crimped state. In one embodiment hereof, female retaining structures (not shown) are disposed within delivery tube 302 for cooperating with retaining elements 28 of stent 12 to minimize longitudinal movement of prosthetic heart valve 10 relative to delivery device 300 during unsheathing and to prevent rotation of prosthetic heart valve 10 relative to delivery tube 302 as delivery device 300 is advanced toward the target location.

Deployment device 306 is extendable through delivery tube 302 and includes a flexible, first or outer shaft 310 extending in a longitudinal direction and a flexible, second or inner shaft 312 extending in the longitudinal direction. In one preferred embodiment, second shaft 312 is telescopically arranged within first shaft 310, such that second shaft 312 is slidable within and relative to first shaft 310. One or more attachment devices 314 are provided on outer shaft 310, at a location marked by X1 (FIGS. 6A and 6B), for coupling outer shaft 310 to a first attachment location 316 provided on a proximal end of sheath 308, and on inner shaft 312, at a location marked by X2 (FIGS. 6A and 6B), for coupling inner shaft 312 to a second attachment location 318 provided on a distal end of sheath 308.

Figure 6A:
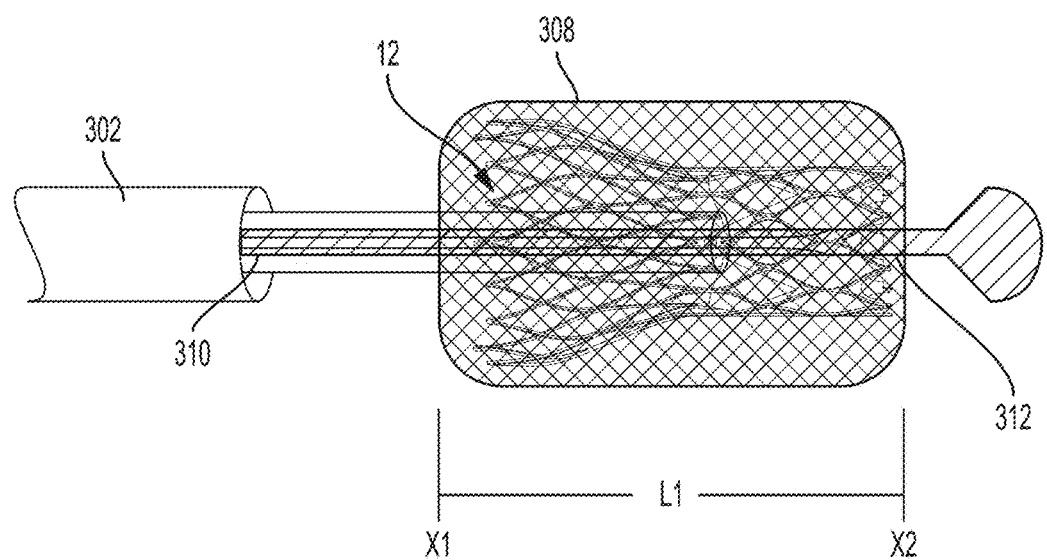
FIG. 6A is a fragmentary, schematic depiction of the system of FIG. 5 in an un-tensioned state.
Figure 6B:
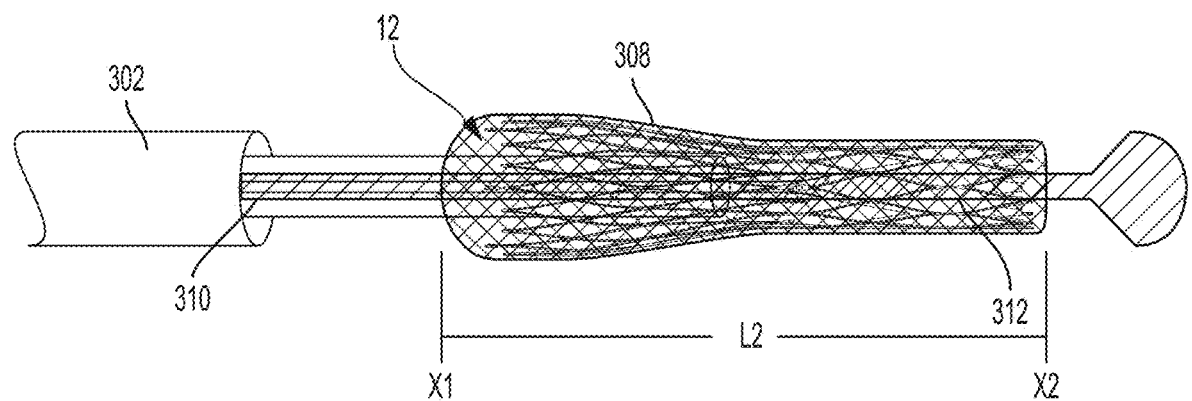
FIG. 6B is a fragmentary, schematic depiction of the system of FIG. 5 in a tensioned state.

As is illustrated in FIGS. 6A and 6B, sheath 308 is an open ended tube or sock-like structure and may be formed of nitinol braid, fabric, or any other strong, yet pliable material that permits blood to flow therethrough. Sheath 308 at least partially surrounds valve 10 when coupled to outer shaft 310 at location X1, and inner shaft 312 at location X2, such that valve 10 will be compressed or crimped when tension is applied to sheath 308. In a first or un-tensioned condition (FIG. 6A), in which no tension or little tension is applied to sheath 308, the distance between X1 and X2 defines a length L1. To compress or crimp heart valve 10, a user slides inner shaft 312 distally relative to outer shaft 310, to a second or tensioned position (FIG. 6B) in which the distance between X1 and X2 defines a second length L2 greater than length L1, thereby applying a tensioning force to sheath 308. Although second shaft 312 is described as telescoping within first shaft 310, it will be understood that second shaft 31:2 may also telescope about first shaft 310, or may be configured to move relative thereto in any manner that increases the length between X1 and X2 in order to apply a tensioning force to sheath 308. Accordingly, after full deployment, if the physician deems that valve 10 is not functioning properly, has jumped, or is otherwise incorrectly positioned, the physician may tension sheath 308, as previously described, to at least partially crimp stent 12 and reposition valve 10. Moreover, in the crimped state, delivery device 302 may be advanced over stent 12 to recapture valve 10 for withdrawal.

Device 300 may optionally include first and second wires 320, 322 disposed within deployment device 306, as shown in FIG. 5, for aiding the user in delivering heart valve 10. Wires 320, 322 are secured to an inner surface of inner shaft 312 in an opposing configuration, and preferably, at or near a distal end of inner shaft 31:2. Accordingly, relative movement between wires 320, 322 will steer flexible inner shaft 312 and flexible outer shaft 310, and in effect heart valve 10, in a desired direction. For example, pulling wire 322 toward trailing end 3:24 relative to wire 320 will cause flexible inner shaft 312 to turn in the direction indicated by arrow B. Conversely, pulling wire 320 toward trailing end 324, relative to wire 322, will cause inner shaft 312 to turn in the direction indicated by arrow A. In order to steer the delivery of valve 10 in another plane, inner shaft 312 may be rotated about its longitudinal axis. The steering mechanism provided by wires 320, 322 reduces tissue trauma as the physician can guide valve 10 through the delivery path as opposed to relying on the tissue to guide the valve 10.

Figure 7:
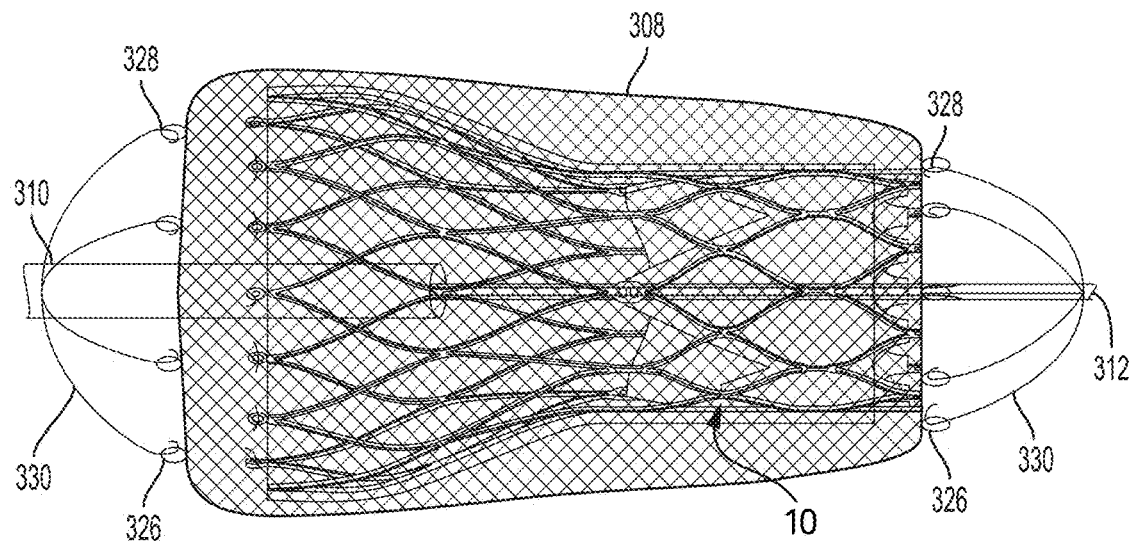
FIG. 7 is a fragmentary side view of an exemplary attachment between a sheath and a delivery device of the system of FIG. 5.

FIG. 7 depicts the attachment, schematically represented in FIG. 5, between deployment device 306 and sheath 308. As shown in FIG. 7, a plurality of loops 326 are provided at the proximal end and the distal end of sheath 308 for removably securing sheath 308 to deployment device 306. Each of loops 326 on the proximal end of sheath 308 is configured to receive a corresponding hook 328 tethered to outer shaft 310 at first attachment location 316 and each of loops 326 on the distal end of sheath 308 is configured to receive a corresponding hook 328 tethered to inner shaft 312 at second attachment location 318. When a slight tension is applied to tethers 330, each hook 328 will engage its corresponding loop 326, thereby coupling delivery device 306 and sheath 308. After tension is released from tethers 330, hooks 328 will be able to disengage from loops 326. After disconnection, deployment device 306 and delivery device 302 may be withdrawn from the body of the patient. In this embodiment, sheath 308 remains sandwiched between stent 12 and the surrounding tissue after delivery device 302 and deployment device 306 have been withdrawn. This aids in sealing valve 10 to the native annulus, thereby reducing paravalvular leak (PVL). Although FIG. 7 illustrates a hook and loop connection, any removeable connection, such as clamps or breakable tethers may be used.

Figure 8:
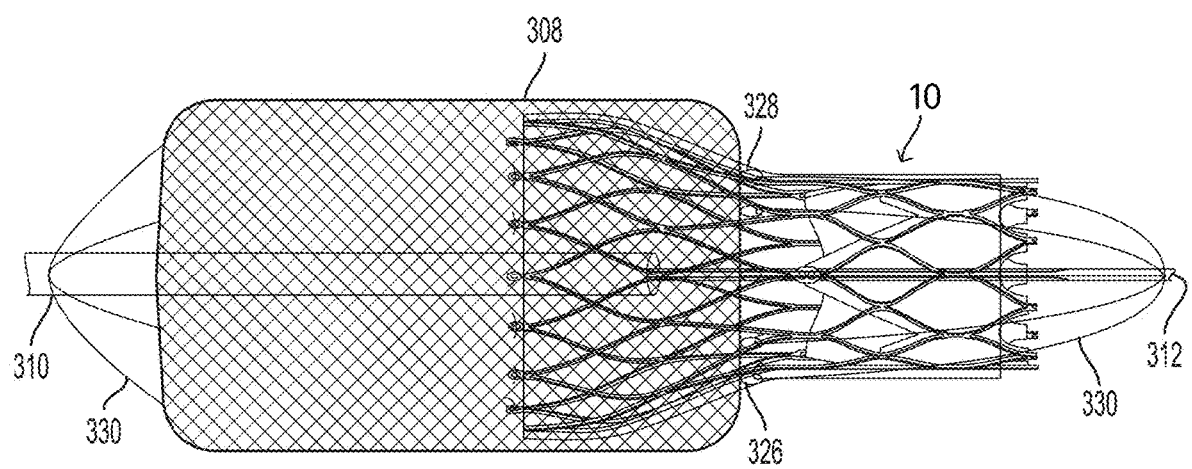
FIG. 8 is a fragmentary side view of another exemplary attachment between a sheath and a delivery device of the system of FIG. 5.

In an alternative embodiment, illustrated by FIG. 8, sheath 308 only partially surrounds stent 12, preferably aortic section 20, which may help in reducing PVL and/or anchoring stent 12 in the native anatomy. As shown in FIG. 8, loops 3:26 are provided on the distal end of sheath 308 for receiving a corresponding hook 328 tethered to inner shaft 312. In contrast to the embodiment illustrated in FIG. 7, the proximal end of sheath 308 is non-removeably connected to outer shaft 310, for example, via tethers 330. When a slight tension is applied to tethers 330, each hook 328 engages its corresponding loop 326, thereby coupling delivery device 306 and sheath 308. However, after tension is released from tethers 330, hooks 328 will disengage from loops 326, thereby disconnecting inner shaft 312 and sheath 308 while tethers 330 maintain a connection between outer shaft 310 and sheath 308. Thus, when annulus section 18 is securely engaged in the valve annulus and when deployment device 306 is withdrawn from the body of the patient, sheath 308 is pulled from between stent 312 and the surrounding heart tissue without dislodging valve 10 from its desired position. An inner surface and/or outer surface of sheath 308 may be lubricated in order to assist sheath 308 in sliding from between the tissue and stent 12 without dislodging valve 10 from its desired position.

To use device 300, a physician places stent 12 around deployment device 306, sheath 308 at least partially around stent 12, and attaches sheath 308 to outer shaft 310 and inner shaft 312. Sheath 308 may then be tensioned by sliding inner shaft 312 distally relative to outer shaft 310 to crimp stent 12 for loading valve 10 into lumen 304 of delivery tube 302. Alternatively, valve 10 and the surrounding sheath 308 may be crimped and loaded into delivery tube 302 using conventional methods.

After delivery device 300 has been loaded, using either a transfemoral or transapical approach, a physician may steer heart valve 10 via wires 320, 322 through a delivery path to a desired location (e.g., within the aortic valve annulus). Once in position, valve 10 may be fully deployed so that the physician can comprehensively analyze valve function and fitment of valve 10 while a slight tension is maintained on tethers 330 so that hooks 328 remain engaged with loops 326. If the physician deems that valve 10 is not properly positioned, the physician may slide inner member 312 away from outer member 310, thereby applying a tensioning force to sheath 308, for crimping stent 12 as previously described. Stent 12 may then be repositioned using guide wires 320, 322. Alternatively, if the physician deems that valve 10 is not functioning properly, delivery tube 302 may be slide over crimped valve 10 to recapture the valve within bore 304 for withdrawal. Advantageously, system 300 provides the physician with the ability to correct improper function or placement of valve 10, after full deployment, such that the valves true function and final placement may be analyzed.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A system, comprising:
   a device for crimping a prosthetic heart valve, comprising:
      a delivery tube extending in a longitudinal direction and having a lumen configured to receive the prosthetic heart valve;
      a deployment device including a first member at least partially received within the lumen of the delivery tube and a second member slidable relative to the first member; and
      a sheath having a first attachment area connected to the first member and a second attachment area connected to the second member; and
   a collapsible and expandable prosthetic heart valve at least partially disposed within the sheath and transitionable between a radially collapsed state and a radially expanded state,
   wherein movement of the first member relative to the second member tensions the sheath and causes the prosthetic heart valve to transition from the radially expanded state to the collapsed state.

2. The system of claim 1, wherein the first attachment area is connected to the first member at a first location, the second attachment area is connected to the second member at a second location, and the second member is telescopically arranged within the first member for transitioning the deployment device between a first condition in which there is a first length between the first location and the second location, and a second condition in which there is a second length greater than the first length between the first location and the second location.

3. The system of claim 1, wherein in the expanded state a diameter of the prosthetic heart valve is larger than a diameter of the lumen of the delivery tube.

4. The system of claim 1, wherein the prosthetic heart valve includes a stent, a cuff and at least one leaflet.

5. The system of claim 2, wherein the deployment device in the first condition exerts a first tension on the sheath and the deployment device in the second condition exerts a second tension on the sheath greater than the first tension, the second tension being sufficient to radially compress at least a portion of the prosthetic heart valve.

6. The system of claim 1, wherein at least one of the first attachment area and second attachment area comprises at least one loop.

7. The system of claim 1, wherein at least one of the first member or the second member includes at least one connector selected from the group of a hook, a clamp, and a tether.

8. The system of claim 7, wherein the tether comprise a breakable braid.

9. The system of claim 1, further comprising a first wire and a second wire opposingly secured within the deployment device for guiding delivery of the heart valve.

10. The system of claim 1, wherein the first attachment area of the sheath is adjacent a proximal end of the sheath and the second attachment area of the sheath is adjacent a distal end of the sheath.

11. The system of claim 1, wherein at least a portion of the sheath is lubricated.

12. The system of claim 1, wherein the sheath is formed of nitinol.

13. A method of crimping a heart valve after the heart valve has been fully deployed from a delivery tube, the method comprising:
   moving a first member connected to a sheath at a first location away from a second member connected to the sheath at a second location, the sheath at least partially enclosing a stent configured to transition between a radially collapsed state and a radially expanded state; and
   transitioning the stent from the expanded state to the collapsed state by applying a tensioning force to the sheath.

14. The method of claim 13, wherein the moving step comprises a telescoping movement.

15. The method of claim 13, further comprising:
   recapturing the stent within a lumen of the delivery tube by crimping, at least a portion of the heart valve to a diameter that is smaller than a diameter of the lumen by which it is recaptured.

16. The method of claim 13, further comprising:
   manipulating at least one of a plurality of wires connected to at least one of the first and second members to steer the delivery of the heart valve.

17. The method of claim 13, further comprising:
   disconnecting at least one of the first member and the second member from the sheath.

18. The method of claim 17, wherein only one of the first member and the second member is disconnected from the sheath.

19. The method of claim 18, further comprising:
   withdrawing the sheath from the body of a patient.

20. The method of claim 17, further comprising:
   withdrawing the first member, the second member, and the delivery device from the body of a patient.

* * * * *